US00PP11564P

United States Patent [19]

Werner et al.

[11] Patent Number: Plant 11,564

[45] Date of Patent: Oct. 10, 2000

[54] PEACH TREE NAMED 'CORINTHIAN ROSE'

[76] Inventors: Dennis James Werner, 268 Kilgore Hall, Horticultural Science Department, North Carolina State University; Steve Martin Worthington; Layne Karlton Snelling, both of 59 Kilgore Hall, Horticultural Science Department, North Carolina State University, all of Raleigh, N.C. 27695-7609

[21] Appl. No.: 09/143,338

[22] Filed: Aug. 28, 1998

[51] Int. Cl.[7] ..... A01H 5/00

[52] U.S. Cl. ..... Plt./196

[58] Field of Search ..... Plt./194, 187, 199, Plt./191, 180, 196

*Primary Examiner*—Howard J. Locker
*Assistant Examiner*—Wendy A Baker

[57] ABSTRACT

A new and distinct cultivar of ornamental peach tree called 'Corinthian Rose' is provided that demonstrates a narrowly columnar growth habit, a vigorous growth rate, dark purple foliage, and an abundance of dark pink colored, double flowers. The new cultivar produces very few fruit, and is intended for use as a Spring flowering ornamental plant in the home landscape.

4 Drawing Sheets

SUMMARY OF THE INVENTION

The new and distinct variety of peach (*Prunus persica* (L.) Batsch) originated as a second generation descendant from a hand pollinated cross of North Carolina Selection NC174RL nectarine (non-patented)×a selection of Japanese 'Pillar' Peach made in 1983 at the Sandhills Research Station at Jackson Springs, N.C. The parent plants used in this hybridization have not been named and released and are unavailable in commerce.

The seeds resulting from this controlled hybridization were germinated in a greenhouse at North Carolina State University, Raleigh, N.C. in the Fall of 1983 and planted in the field in Spring of 1984. These trees were grown to maturity; trees were self pollinated in Spring of 1988, and the resultant seed was harvested in August 1988. This seed was sown directly in the field in November 1988, and seedlings flowered in 1991. One seedling, designated NC174RL×Pil-248, was selected for its dark purple foliage color, narrowly columnar growth habit, and heavy production of dark pink double flowers.

During 1993 and 1996, the original plant selection was propagated asexually by grafting of vegetative buds onto a peach rootstock, cultivar 'Lovell', at the Sandhills Research Station. A grafted tree of the variety was established at the North Carolina State University Lake Wheeler Field Laboratory Research Station in Raleigh, N.C. Subsequently, a larger test planting has been established with asexually multiplied plants at the Sandhills Research Station, at the above noted location.

The new variety has routinely been asexually multiplied by grafting, specifically 'T' and chip budding. It readily forms a graft union with 'Lovell' peach rootstock and resumes normal growth. During all asexual propagation, the characteristics of the original plant have been maintained and no aberrant phenotypes have appeared.

Test plantings at the two research station locations noted above, which vary considerably in soil and climatic conditions, demonstrate this variety to be widely adapted to differing soil and climatic conditions.

Plants and fruit of this new variety differ phenotypically from its antecedents. The new variety produces dark purple leaves and dark pink double flowers, differing from the single pink flowers of NC174RL and the double pink and white variegated flowers, and green leaves of the Japanese 'Pillar' Peach antecedent. Growth habit is narrowly columnar, and fruit are pubescent (peach), distinguishing it from the NC174RL nectarine antecedent. Fruit of this new variety are small and of poor quality, and are of no commercial importance.

Plants of the new variety are very vigorous and grow rapidly after establishment of trees in the field. Young trees have averaged 3-4 feet of growth per year. A four-year-old tree measured in Raleigh, N.C. was 14 feet in height and 4.3 feet in spread, with spread measured 6 feet from ground level. Trunk diameter (girth) was 4.1 inches, measured one foot from ground level. Plants are narrowly columnar in growth habit. The branch angles between the trunk and lateral branches of 'Corinthian Rose' measure between 5 to 20 degrees, in comparison to non-columnar peach varieties such as 'Contender', which typically measure between 35 to 50 degrees.

Flowering sometimes occurs in the second year of growth, but more commonly trees begin flowering in the third year after establishment. Flowers are fully double, dark pink, and very attractive. Flowering usually begins in mid to late March in Raleigh, N.C.; the date of first bloom typically occurs from March 15 to March 30. Full bloom typically occurs from March 25 to April 10, depending on weather conditions. Bloom duration is typically 10–14 days, and individual flowers last about 7–10 days, depending on temperature during bloom. The chilling requirement is estimated to be 950 hours below 4 C., based on comparison of flowering time to peach varieties 'Contender' (unpatented), 'Winblo' (unpatented), and 'Clayton' (unpatented) at the Raleigh, N.C. test site.

While 'Corinthian Rose' is a self-fruitful peach variety, fertility of flowers is poor, and fruit set is generally low in most years, for unknown reasons, unrelated to the pollination requirements of the tree. It is estimated that less than 1% of flowers produced set fruit. Fruit are very small, bitter tasting, and of no horticultural importance. Fruit ripen in mid to late August in Raleight, N.C.

'Corinthian Rose' possesses double, rose colored flowers, and dark purple leaves, distinguishing it from 'Corinthian White' (co-pending U.S. Plant patent application Ser. No. 09/146,219), which possesses double, white colored flowers and green leaves. 'Corinthian Rose' differs from 'Corinthian Mauve' (co-pending U.S. Plant patent application Ser. No. 09/146,220) in having dark purple leaves and rose colored flowers in contrast to the green leaves and mauve colored flowers of 'Corinthian Mauve', 'Corinthian Rose' differs from 'Corinthian Pink' (co-pending U.S. Plant patent application Ser. No. 09/143,339) in having dark purple leaves and rose colored flowers in contrast to the light purple leaves and light pink flowers of 'Corinthian Pink'.

The new variety has been named the Corinthian Rose cultivar.

BRIEF DESCRIPTION OF THE DRAWINGS

The accompanying photographs show typical specimens of the entire tree during and after flowering, and close-up pictures of the flowers in color as nearly true as it is reasonably possible to make in a color illustration of this character.

DETAILED DESCRIPTION OF THE NEW VARIETY

Figure 1:
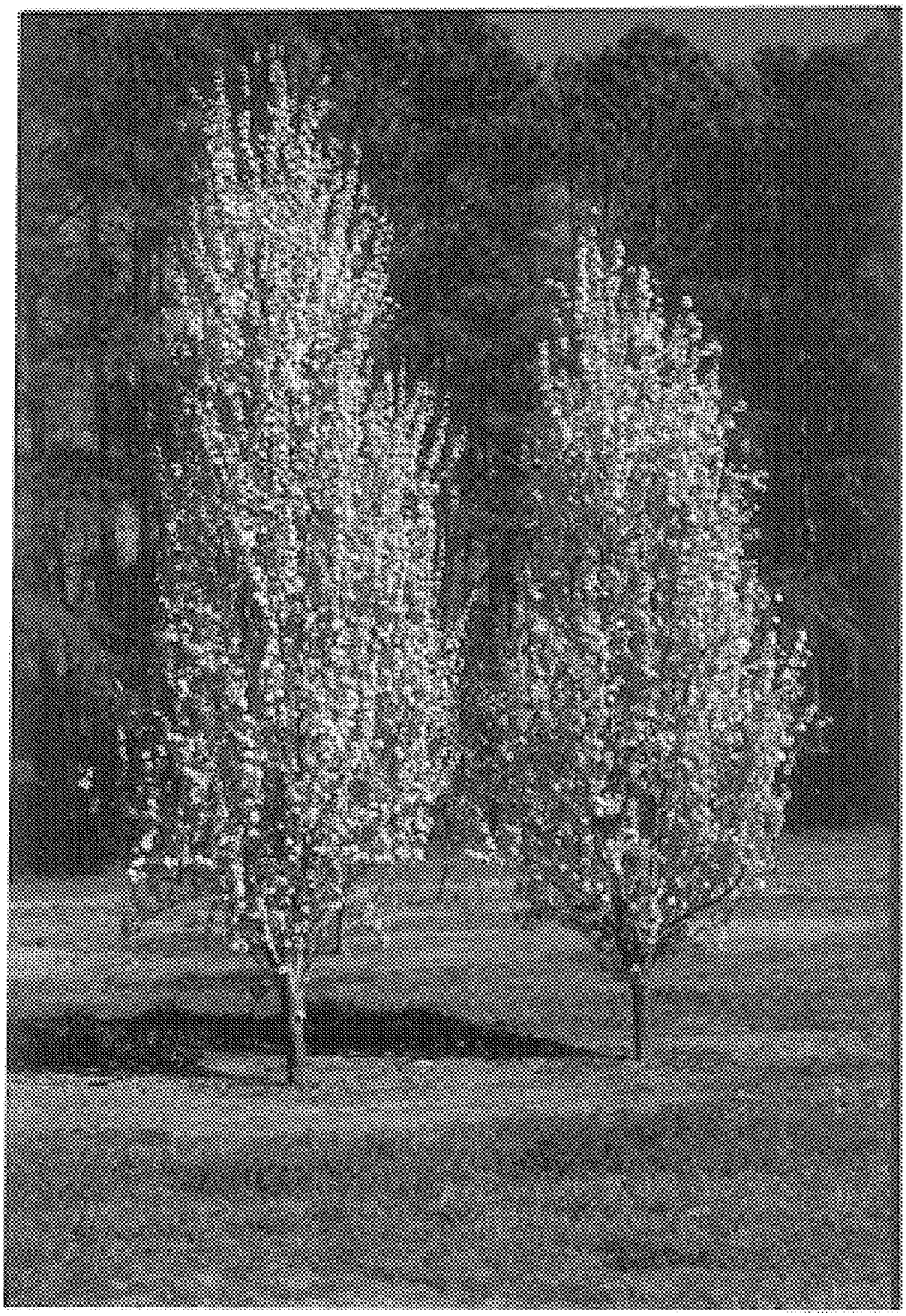
FIG. 1 shows a four-year-old tree of 'Corinthian Rose' (left-hand-side) in comparison to 'Corinthian Mauve' (right-hand-side) in full bloom at Raleigh, N.C., showing the narrowly columnar tree architecture, flower color, and heavy flowering characteristics.
Figure 2:
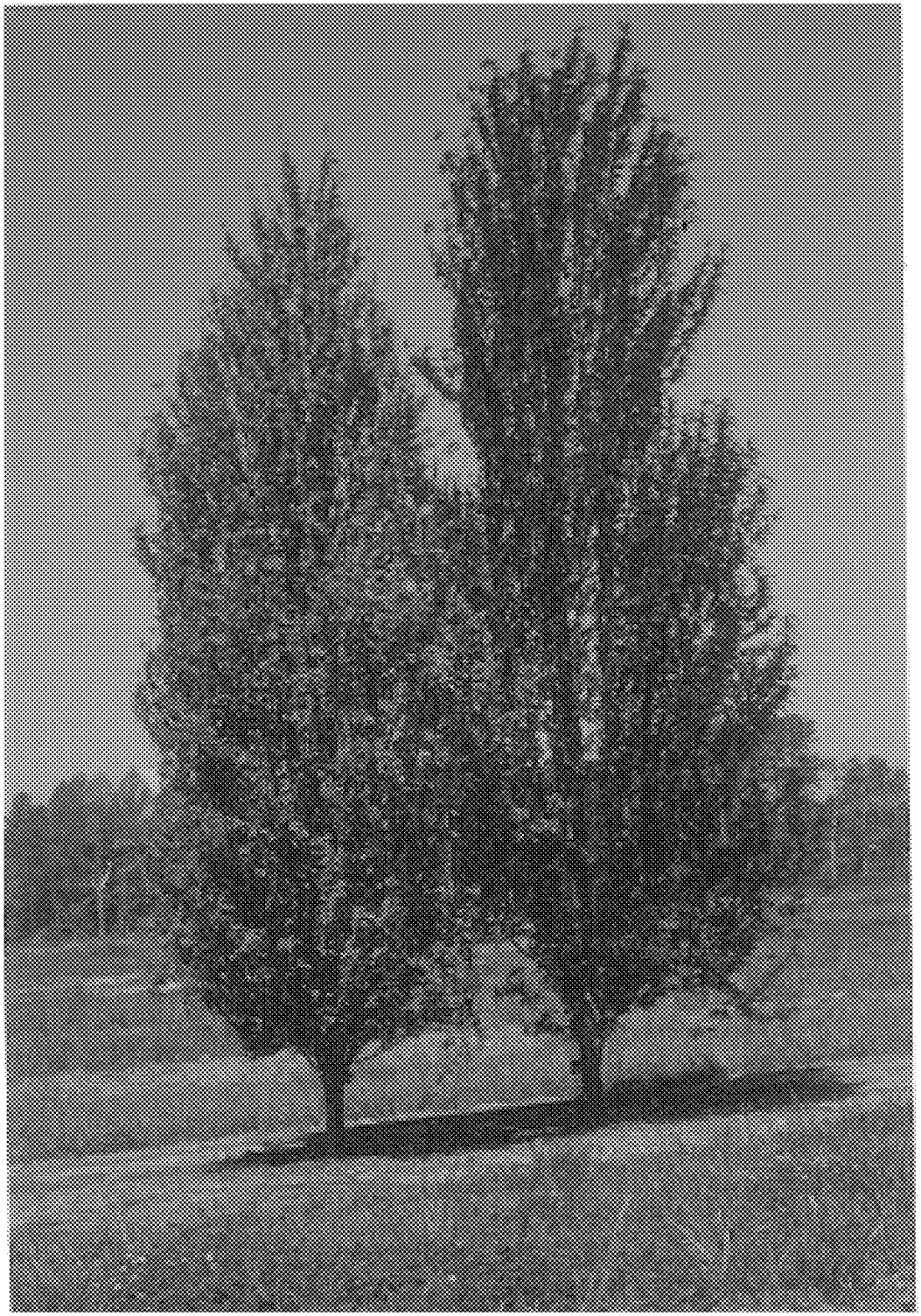
FIG. 2 shows a four-year-old tree of 'Corinthian Rose' (right-hand-side) in comparison to 'Corinthian Mauve' (left-hand-side) taken after flowering, showing the narrowly columnar tree architecture and the overall foliage color.
Figure 3:
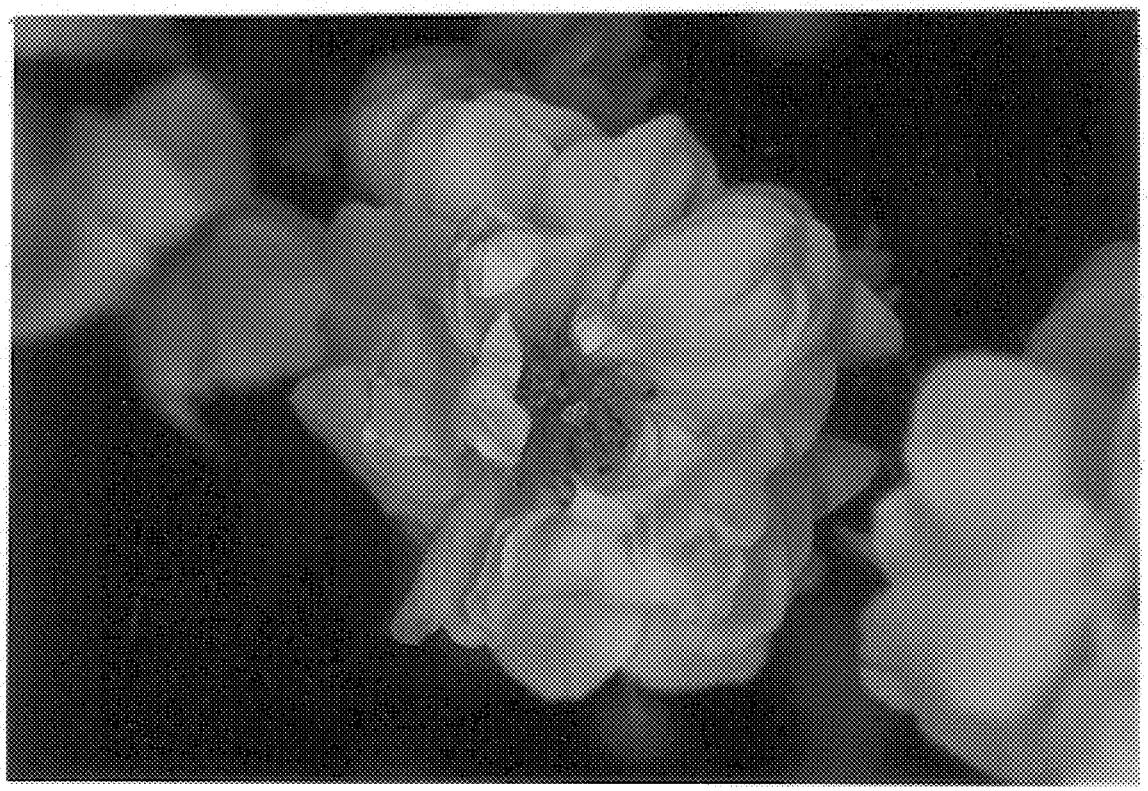
FIG. 3 shows a close up photograph of the flower of 'Corinthian Rose', showing the double flower structure, and the dark-pink flower color.
Figure 4:
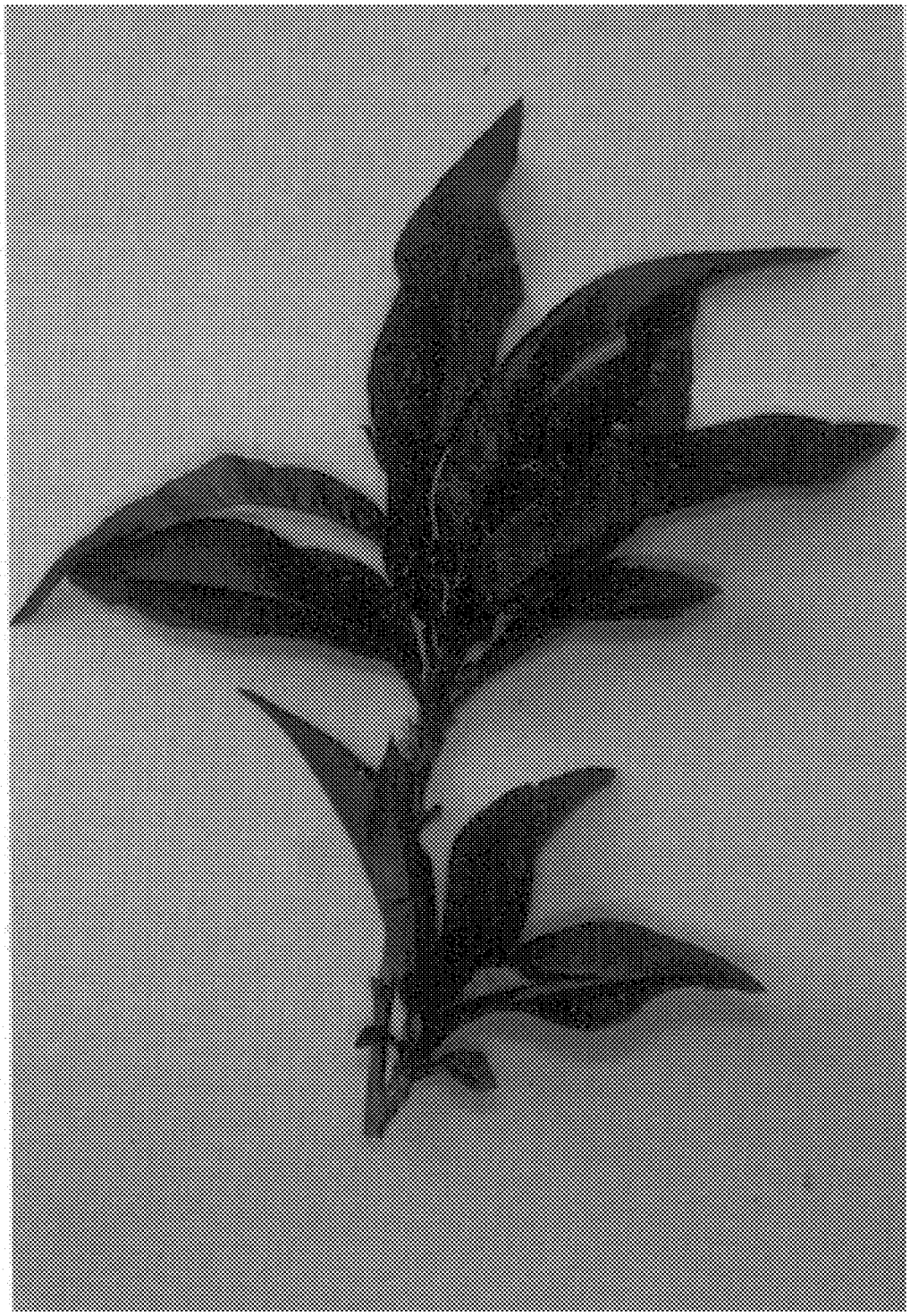
FIG. 4 is a close-up picture, taken May 18, 2000, showing the newly formed dark purple leaves of 'Corinthian Rose' attached to a rapidly growing shoot.

The following is a detailed description of the botanical and pomological characteristics of the subject peach. Color data are presented in Royal Horticultural Society Colour chart designations. Where dimensions, sizes, colors and other characteristics are given, it is to be understood that such characteristics are approximations of averages set forth as accurately as practicable.

The descriptions reported herein are from specimens grown at Raleigh, N.C. unless otherwise noted.

Tree:
- *Size.*—Large. 14–16 ft. in height after four years of growth.
- *Vigor.*—Very vigorous.
- *Growth.*—Narrowly columnar.
- *Production.*—Low.
- *Pest resistance.*—susceptible to peach tree borer, moderately resistant to bacterial leaf spot (Sandhills Research Station observations).

Trunk:
- *Size.*—Medium.
- *Texture.*—Medium to rough.
- *Color.*—Gray-green (197-A).

Branches:
- *Size.*—Medium.
- *Surface.*—Smooth (new) to medium rough (old).
- *Lenticels.*—Medium size. Medium number.
- *Color.*—Bright green with slight red blush on sun-exposed sides (Actively growing new growth). Dormant one-year-old shoots gray-red (178-B). Dormant two-year-old shoots gray-brown (199-A).

Foliage:
- *Leaves.*—Large. Mature leaf length 11.1 cm; width 3.8 cm.
- *Form.*—Lanceolate. Acutely pointed. Leaf base medium pointed, cuneate.
- *Thickness.*—Medium.
- *Texture.*—Smooth to slightly rugose.
- *Margin.*—Crenate.
- *Stipules.*—Present. Small.
- *Pubescence.*—Absent on both lower and upper surface.
- *Venation.*—Pinnate.
- *Petiole.*—Medium length.
- *Glands.*—Average number 3. Varies from 2 to 5. Located on base of leaf and upper portion of petiole. Reniform.
- *Color.*—Upper surface — Dark purple 187A (newly emerged) to red-purple 187B (mature leaf).
- *Lower surface.*—R.H.S. 187B.
- *Density.*—Dense.

Flower buds:
- *Size.*—Large.
- *Length.*—Medium.
- *Shape.*—Plump, typical of peach, slightly tapered at apex.
- *Color.*—Light brown.

Flowers:
- *Date of first bloom.*—March 15 to March 30. Varies yearly due to weather conditions.
- *Date of full bloom.*—March 25 to April 10. Varies yearly due to weather conditions.
- *Size.*—Large, double, showy.
- *Diameter.*—38 mm (average of 5 flowers).
- *Pedicel length.*—15 mm.
- *Color.*—Dark pink (red 56C, newly emerged flowers), red 68C, (mature flowers), R.H.S. 183A (calyx/sepals).
- *Reproductive organs.*—Stamens — erect, numerous. Pistils — usually one. Pollen — normal and abundant. Bright yellow.
- *Number of flowers per bud.*—One.
- *Number of petals per flower.*—Average 27.4.
- *Petal shape.*—Typical of peach.
- *Fertility.*—Self-fertile.

Fruit:
- *Maturity.*—Late. Mid to late August.
- *Size.*—Very small. Less than 3.0 cm diameter.
- *Fruit weight.*—Average of 5 fruit weighed on May 25, 2000, 13.9 grams.
- *Form.*—Slightly oblong.
- *Suture.*—Shallow.
- *Pubescence.*—Heavy.
- *Skin color.*—Yellowish-green with light red blush.
- *Flesh color.*—White.
- *Stone.*—Small, freestone.
- *Eating quality.*—Very poor.
- *Users.*—None.

The Variety

The most distinctive features of the variety are its narrowly columnar growth habit, its dark purple foliage color, and its double (multiple petals) dark pink flowers.

We claim:

1. A new and distinct variety of ornamental peach tree, substantially as illustrated and described, characterized by its narrowly columnar growth habit, dark purple foliage color, and large double dark pink flowers.

* * * * *